US006048725A

United States Patent [19]
Shimada et al.

[11] Patent Number: 6,048,725
[45] Date of Patent: *Apr. 11, 2000

[54] RECOMBINANT HUMAN IMMUNODEFICIENCY VIRUS PRODUCING CELL LINES

[75] Inventors: Takashi Shimada, Tokyo; Katsuhiko Akiyama, Ibaraki-ken; Hidekazu Kuma, Ibaraki-ken; Yosuke Suzuki, Ibaraki-ken, all of Japan

[73] Assignee: Hisamitsu Pharmaceutical Co., Inc., Saga, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/913,705
[22] PCT Filed: Mar. 15, 1996
[86] PCT No.: PCT/JP96/00653

§ 371 Date: Sep. 12, 1997

§ 102(e) Date: Sep. 12, 1997

[87] PCT Pub. No.: WO96/29393

PCT Pub. Date: Sep. 26, 1996

[30] Foreign Application Priority Data

Mar. 17, 1995 [JP] Japan ................................ 7-097410

[51] Int. Cl.[7] .................................................. C12N 15/00
[52] U.S. Cl. ................... 435/366; 435/172.1; 435/172.3; 435/320.1; 424/93.2; 424/93.21; 424/93.6; 424/93.7; 935/22; 935/23; 935/32; 935/55; 935/56; 935/57; 935/66; 935/70; 935/71
[58] Field of Search ............................. 435/240.1, 240.2, 435/320.1, 173.1, 172.3, 366; 935/22, 23, 32, 55, 56, 57, 66, 70, 71; 424/93.2, 93.21, 93.6, 93.7

[56] References Cited

PUBLICATIONS

Shimida et al., *J. Clin. Invest.*, v. 88, pp. 1043–1047, 1991.
Himuna, Y. et al., *Proc. Natl. Acad. Sci.*, v. 78, 6476–6480, 1981.
Sullenger, B.A. et al., *Cell*, v. 63, pp. 601–608, 1990.
Chatterjee, S. et al., *Science*, v. 258, pp. 1485–1488, 1992.
Stevelo, K.M. et al., *Virology*, v. 190, pp. 176–183, 1992.
Hope, T.J. et al., *J. Virol.*, v. 66, pp. 1849–1855, 1992.
Richardson, J.H. et al., "Vectors based on HIV." HIV. Editor: Karn Jonathan, vol. 1, 1995, pp. 89–113.
Louis D. St. et al., "Construction and characterization of HIV–1 retroviral vectors and replication–defective HIV–1 packaging cell lines." IXTH International Conference on AIDS and The IVTH STD World Congress, Jun. 1993, Berlin Germany, p. 244.
Poznansky M. et al., "Gene Transfer into Human Lymphocytes by a Defective Human Immunodeficiency Virus Type 1 Vector." vol. 65, No. 1, Jan. 1, 1991, pp. 532–536.

Bosselman R.A. et al. "Replication–Defective Chimeric Helper Proviruses and Factors Affecting Generation of Competent Virus: Expression of Moloney Murine Leukemia Virus Structural Genes Via The Metallothionein Promoter" Molecular and Cellular Biology, vol. 7, No. 5, May 1, 1987.

Shinya E. et al. "A safe HIV vectors packaging system using the U3 deficient LTR.", Gene Therapy Meeting, Sep. 21–25, 1994, Cold Spring Harbor, p. 150.

Mclachlin, J. R. et al., "Retroviral–Mediated Gene Transfer." Progress in Nucleic Acid Research and Molecular Biology, vol. 38, 1990, pp. 91–135.

Carroll R. et al., "A Human Immunodeficiency Virus Type 1 (HIV–1)–based retroviral vector system utilizing stable HIV–1 packaging cell line." Journal of Virology, vol. 68, No. 9, Sep. 1994, pp. 6047–6051.

Haselhorst D. et al., "Stable packaging cell–lines and HIV–1 based retroviral vector Systems." Gene Therapy, vol. 1, No. Suppl. 2, 1994. p. S14.

Richardson et al. "Helper Virus–Free Transfer of Human Immunodeficiency Virus Type 1 Vectors", Journal of General Virology, vol. 76, Part 3 (Mar. 1995) pp. 691–696. GR1.J6.

Strair et al. "Recombinant Retroviral Systems for the Analysis of Drug Resistant HIV", Nucleic Acids Research, vol. 21, No.20 (Oct. 11, 1993) pp. 4836–4842. QP620.N8.

Richardson et al. "Packaging of Human Immunodeficiency Virus Type 1 RNA Requires cis–Acting Sequence Outside the 5'Leader Region", Journal of Virology, vol. 67, No. 7(Jul. 1993), pp. 3997–4005, QR 355.J65.

*Primary Examiner*—Jeffrey Stucker
*Attorney, Agent, or Firm*—Morrison & Foerster, LLP

[57] ABSTRACT

Recombinant human immunodeficiency virus producing cell that is obtained by introducing into an animal cell a recombinant human immunodeficiency virus helper plasmid containing at least the sequences of gag, pol and env genes encoded by a human immunodeficiency virus genome and being deficient of a packaging signal and which sustains said genes stably.

The human immunodeficiency virus producing cell of the invention is capable of large-scale and consistent preparation of HIV vectors more efficiently than in the prior art.

10 Claims, 4 Drawing Sheets

CELL LINES OBTAINED IN EXAMPLE 3

NEGATIVE CONTROL GROUP

RECOMBINANT HUMAN IMMUNODEFICIENCY VIRUS PRODUCING CELL LINES

TECHNICAL FIELD

This invention relates to recombinant human immunodeficiency virus vectors (hereinafter, HIV vectors), a process for producing said vectors, and productive cells capable of sustaining said vectors stably.

BACKGROUND ART

The recent rapid advances in genetic engineering triggered the development of various techniques in molecular biology. This has been commensurate with remarkable advances in the analysis of genetic information and the unravelling of functions of genes and many attempts are being made to exploit these achievements in practical therapeutic settings. One of the areas that have seen the most remarkable advances is that of gene therapy. Etiological genes of various genetic diseases have been discovered and deciphered on one hand, and procedures for transferring such genes into cells by physical and chemical techniques have been developed on the other; as a result, gene therapy has progressed from the stage of preclinical experimentation to practical clinical applications.

Depending on the type of cells (target cells) for gene transfer, gene therapy is classified as either germline cell gene therapy or somatic cell gene therapy. Another way of classification is into augmentation gene therapy which involves the addition of a new (normal) gene, with an abnormal (etiological) gene left intact, and replacement gene therapy for replacing an abnormal gene by a normal gene. At the present stage, only augmentation gene therapy of somatic cells is being practised in consideration of ethical and technological restraints. More specifically, a method of gene therapy in current practice is one by autotransplantation (ex vivo gene therapy) in which a target cell is taken out of the patient and a gene to be inserted is transferred into the target cell, which is then replaced into the patient's body. A method under review for future possibility is one that involves direct gene administration into the patient (in vivo gene therapy).

One of the major technological challenges for the clinical application of the above-described gene therapy is the development of a method for introducing an exogenous gene into a target cell in an efficient and consistent way. In the early eighties, physical techniques such as microinjection were attempted; however, these methods were not eventually commercialized for several reasons such as low gene transfer efficiency, incapability to achieve consistent transfer and the limitations of the then available technology of large-scale cell cultivation. It was not until a recombinant virus (viral vector) for inserting an exogenous gene efficiently into a target cell was later developed that the clinical application of gene therapy became a possibility.

In the United States of America, about 70 protocols of gene therapy have been approved and in practice no fewer than 200 patients are presently undergoing gene therapy. A mouse leukemia virus (MoMLV, or Moloney's murine leukemia virus) vector is the most commonly used means of gene transfer. MoMLV is a kind of retrovirus and infects a host cell if the envelope on its surface binds specifically to the receptor on the surface of the host cell. Recombinant MoMLVs are capable of gene transfer into different cell species depending on the type of envelope and are classified as, for example, ecotropics which infect only rodents and amphotropics which infect both rodents and human cells.

Preparing a recombinant MoMLV vector first requires the construction of two plasmids, one being a helper plasmid which comprises gag, pol and env genes to be coded in a MoMLV genome and a promoter for driving these genes, and the other being a vector plasmid having the terminal repeated sequence (LTR) of MoMLV inserted at both ends of the gene acting as a drug. In this case, for the purpose of preventing the production of a wild type of virus, a packaging signal which is a signal sequence for packaging the gene into the particle of a virus is preliminarily removed from the helper plasmid. In contrast, the packaging signal is contained in the vector plasmid. In many cases, a reporter gene for recognizing or selecting only the cell transfected with the viral vector is inserted into the gene sequence of the vector plasmid. Cotransfecting the cell with these two kinds of gene allows a recombinant viral vector to be produced within the supernatant of culture.

In recent years, cell lines called "packaging cells" have been established as means for achieving more efficient preparation of MoMLV vector. These are cell lines in which the helper plasmid and/or vector plasmid which are necessary for preparing the MoMLV vector have been integrated stably into the cellular genomic DNA. The use of such cell lines offers many advantages, among which the following are worth particular mention:

(1) the cumbersomeness of transfection in the preparation of a viral vector is eliminated;
(2) compared to transfection procedures typified by a calcium phosphate procedure which are limited in the efficiency of gene transfer into a cell, using packaging cells into all of which a gene of interest has already been transferred Is advantageous for preparing a viral vector of high potency;
(3) if transfection is performed in several lots by the calcium phosphate procedure, the gene transfer efficiency scatters between lots, so viral vectors of a constant potency cannot be supplied consistently but this is not the case with the preparation procedure using packaging cells and the scattering of gene transfer efficiency is small; and
(4) in the calcium phosphate procedure, preparing a large quantity of viral vectors requires a correspondingly large volume of plasmids for transfection but there is no need for this if the packaging cells are used.

Because of these and other advantages, the use of the packaging cells is presently the most common method of preparing MoMLV vector.

Another property of MoMLV vector is the lack of host specificity. This property indicates that various cells can be the target cell of MoMLV vector, making it possible to use the vector in association with various diseases. On the other hand, the inherent lack of host specificity which is the property of the viral vectors under consideration makes their administration to the human body difficult, As a matter of fact, if these viral vectors are to be utilized for therapeutic purposes, certain considerations must be given to the method of administration. For instance, when they are to be administered to hemocytes, the method in current use comprises the steps of taking the cell to be treated out of the human body, performing gene transfer and thereafter putting the cell back into the human body (ex vivo gene transfer); however, this technique requires special equipment and hence can be employed for therapeutic purposes in only limited facilities. If the viral vectors are to be administered to cells that have settled in certain organs or tissues, the method currently used is topical administration to the organ or tissue to be treated; however, this approach has several problems such as the need to perform a surgical operation for enabling the topical administration.

Tissue specific viral vectors have been developed as a means for solving the aforementioned problems. An HIV vector is a kind of tissue specific viral vectors capable of specific gene transfer into CD4 positive cells and utilizes the ability of HIV envelope protein gp120 to bind specifically to the CD4 protein on the surfaces of CD4 positive T lymphocytes during infection (Shimada, T., et al, J.Clin. Invest. 88, 1043, 1991). Diseases that are anticipated to be treated by gene therapy using this viral vector include acquired immunodeficiency syndrome (AIDS) and adult T-cell leukemia (ATL) which have particularly high mortality rates because CD4 positive lymphocytes are the etiological agent and for which there are no established methods of treatment.

Acquired immunodeficiency syndrome (AIDS) is a disease caused by infection of CD4 positive lymphocyes with human immunodeficiency virus (HIV) and, as the result of severe damage to cell-mediated immunity, it triggers the onset of various opportunistic infections, lymphoma, neuropathy, etc. The presently used therapeutics of HIV are drugs categorized as reverse transcriptase inhibitors of a nucleotide class and 3'-azido-2',3'-dideoxythymidine (AZT), 2',3'-dideoxyinosine (ddI), 2',3'-dideoxycytidine (ddC), etc. are used either independent-ly or in combination. However, none of these drugs have an ability to reject already infected cells; in addition, they have big problems such as the one of causing severe side effects including significant bone marrow suppression and symptoms in digestive organs, as well as the occurrence of drug-resistant viral strains; under the circumstances, there is a strong need to develop a new type of drug that is more efficacious, has less side effects and permits fewer resistant viral strains to occur.

Speaking of adult T-cell leukemia (ATL), this is a conceptual disease proposed by Uchiyama et al. (Uchiyama, T. et al., Blood, 50, 481–492, 1977) and HTLV-1 is considered to be the etiological virus of the disease (Hinuma, Y. et al., Proc. Natl. Acad, Sci. USA, 78, 6476–6480, 1981); however, much remains to be elucidated as regards the mechanism of the onset of ATL and the mechanism of growth of ATL cells. As far as acute lymphocytic leukemia is concerned, combinations of chemotherapy with radiotherapy and/or bone marrow transplantation have proven today to cause a fairly high incidence of remission or healing. However, as for ATL, the treatment by those methods has not achieved satisfactory results and the development of a new therapeutic method is in urgent demand.

In recent years, the applicability of gene therapy to these refractory diseases has been under preclinical review. As for AIDS, various treatment systems that take advantage of the mechanism of HIV replication in elegant ways have been proposed and they include: using RNA decoys such as TAR and RRE decoys in order to suppress the actions of Tat and Rev which are believed to be potent accelerators of HIV replication (Sullenger, B. A. et al., Cell 63, 601, 1990); hybridizing with HIV mRNA or DNA by means of an antisense oligonucleotide (Chatterjee, S. et al., Science, 258, 1485, 1992); cutting the RNA of HIV by means of a ribozyme (Stevelo, K. M. et al., Virology, 190, 176, 1992) ;and using a transdominant mutant to suppress the function of proteins essential to HIV replication (Hope, T. J. et al., J. Virol, 66, 1849, 1992).

As for ATL, a system is under review that integrates a thymidine kinase gene in a human simplex herpes virus into an ATL cell, said gene being expressed such that only the ATL cell is specifically killed by means of ganciclovir (Kazunori Imada and Taku Uchiyama, ZOKETSU INSHI (Hematopoietic Factors), 5, 4, 501–503, 1994).

As already mentioned, the HIV vector has very high utility as a tissue specific viral vector but it has several problems with the procedure of preparation. The currently employed method of preparing HIV vector is by cotransfecting COS cells with a helper plasmid and a vector plasmid just prior to use. However, as noted hereinabove, the transfection procedures typified by a calcium phosphate method has various problems including (1) cumbersome operations, (2) limited efficiency of gene transfer, (3) lot-to-lot fluctuations in the efficiency of gene transfer and (4) the need for large-scale preparation of plasmids. Hence, it has been necessary to establish a method capable of more efficient and consistent preparation of the HIV vector.

Although the HIV vector holds promise for use as a tissue specific viral vector, the method of its preparation involves many problems and the currently employed method is by cotransfection with a helper plasmid and a vector plasmid just prior to use. However, several big problems exist with this method, as summarized below: (1) transfection efficiency is variable from lot to lot, so the potency of the vector fluctuates to make consistent supply impossible; (2) due to the cumbersomeness of transfecting operations, vectors cannot be prepared in large quantities; and (3) if large amounts of HIV vector are to be prepared, correspondingly large amounts of plasmid vector have to be prepared. As for MoMLV vector, packaging cell lines have already been established that have a helper plasmid and a vector plasmid incorporated stably into genomic DNA; however, the establishment of packaging cell lines has not yet been accomplished for HIV vector. A reason for this would be that compared to cells for sustaining MoMLV which are mouse-derived such as murine 3T3 cells, human-derived cells have to be used as cells for sustaining HIV vector.

Disclosure of Invention

The present invention has been accomplished under these circumstances and has as an object providing recombinant human immunodeficiency virus producing cells for large-scale and consistent preparation of HIV vector.

As the result of the intensive studies conducted in order to attain the stated object, the present inventors found that a certain kind of recombinant human immunodeficiency virus helper plasmid containing at least the sequences of gag, pol and env genes encoded by a human immunodeficiency virus genome and which is deficient of a packaging signal sequence could be introduced into animal cells and sustained there stably, and completed the present invention.

Thus, the present invention provides a recombinant human immunodeficiency virus producing cell that is obtained by introducing into an animal cell a recombinant human immunodeficiency virus helper plasmid containing at least the sequences of gag, pol and env genes encoded by a human immunodeficiency virus genome and being deficient of a packaging signal and which sustains the introduced genes stably.

The present invention also provides a recombinant human immunodeficiency virus helper plasmid for establishing said recombinant human immunodeficiency virus producing cell which contains at least the sequences of gag, pol and env genes encoded by a human immunodeficiency virus genome and which has a promoter inserted upstream of said gene sequences.

According to one embodiment of the present invention, the recombinant human immunodeficiency virus helper plasmid comprises a plasmid containing at least the sequences of gag and pol genes encoded by a human immunodeficiency virus genome and which has a promoter inserted upstream of said gene sequences, as well as a plasmid containing at least the sequence of env gene encoded by the human immunodeficiency virus genome and which has a promoter inserted upstream of said gene sequence.

According to another embodiment of the present invention, the recombinant human immunodeficiency virus helper plasmid comprises a plasmid containing at least the sequence of gag gene encoded by a human immunodeficiency virus genome and which has a promoter inserted upstream of said gene sequence, a plasmid containing at least the sequence of pol gene encoded by the human immunodeficiency virus genome and which has a promoter inserted upstream of said gene sequence, as well as a plasmid containing at least the sequence of env gene encoded by the human immunodeficiency virus genome and which has a promoter inserted upstream of said gene sequence.

The present invention also provides a method of establishing packaging cells using said plasmid vectors, as well as a process for producing recombinant HIV vectors using said packaging cells.

BEST MODE FOR CARRYING OUT THE INVENTION

The constitution and preferred embodiments of the present invention will now be described in detail.

The packaging cells of the invention can be prepared by the following procedure. A helper plasmid of the structure shown in FIG. 1 is constructed by a known method; as shown, gag, pol and env genes of the wild HIV genome sequence are flanked upstream thereof by a cytomegalovirus derived promoter which is a driver of these genes, and a neomycin resistance gene which is a reporter gene and a promoter of human simplex herpes virus-derived thymidine kinase are inserted downstream of the sequences of gag, pol and env genes and the group of such genes are incorporated into an expression vector, thereby constructing the helper plasmid.

The promoter for driving gag, pol and env genes contained in the helper plasmid is not limited to the cytomegalovirus derived promoter and may be replaced by others such as a B19 derived promoter and a promoter of human simplex herpes virus derived thymidine kinase. The reporter gene also is not limited to any particular types and besides a neomycin resistance gene, other reporter genes such as a hygromycin resistance gene may be used in accordance with the specific use and object.

Figure 1:
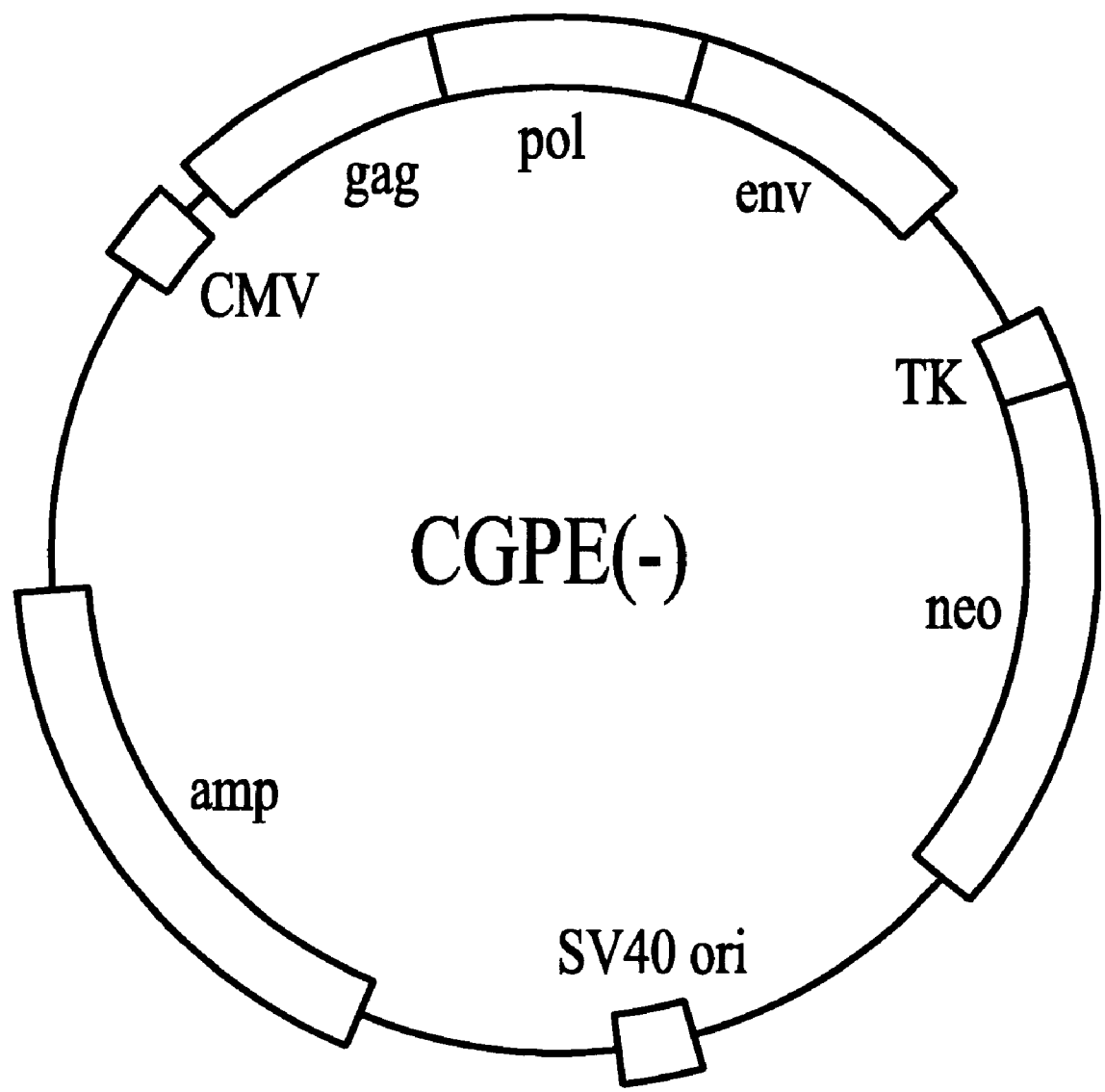
FIG. 1 is a diagram showing the structure of helper plasmid CGPE(-)

No case has been reported to date that wild HIV came into existence as the result of use of the helper plasmid shown in FIG. 1. For the purpose of assuring enhanced safety, the packaging cells can also be established by reconstructing gag, pol and env genes in two or three plasmids and cotransfecting a target cell with the plasmids.

The thus constructed helper plasmid is subsequently used to transfect cells, which may be of any types including COS cells, cancer cells such as HeLa cells and lymphocytic cells such as H9 and CEM. The method of transfection also is not limited in any way and a calcium phosphate procedure, a lipofection and various other methods known to the skilled artisan may be employed. The transfected cells are cultured for several days, detached from the culture dish and reseeded in a fresh dish. Several hours later, a neomycin analogue G418 is added in a suitable amount into the culture solution and only the cells transformed with the exogenous gene are selected. If the hygromycin resistance gene is contained as a reporter gene in any one of the sequences in the helper plasmid, a suitable amount of hygromycin is also added to the culture medium. Following cultivation in a $CO_2$ incubator for 7–10 days, the resulting colonies are picked up one by one and reseeded separately in fresh dishes. Following cultivation for additional 7–10 days, the supernatants of the culture are stored for subsequent screening.

Packaging cells for producing the HIV vector may be selected by the following procedure.

With part of the above-described supernatant of culture used as a sample, the expressability of p24 protein and/or gp120 protein is quantitated by an ELISA method to perform primary screening. Other methods of quantification may be employed, such as analysis by FACS (fluorescein activated cell sorting) using a fluorescent antibody or gene analysis by Southern blotting or Northern blotting. Clones found to have high protein expressability by one of these quantification methods are stored.

Recombinant HIV vectors are prepared using the clones obtained by primary screening and their potency is assayed to perform secondary screening. Each of these clones is transfected with a vector plasmid by a known method. The vector plasmid is prepared by deleting gag, pol and env genes from a wild HIV genomic sequence, inserting a reporter gene sequence into the vacant region and incorporating the resulting gene group into an expression vector. The reporter gene to be inserted is not limited to any particular type and may be selected from among drug resistance genes such as a neomycin resistance gene and a hygromycin resistance gene, or genes coding cell surface antigens such as CD4 protein. Following 2-day cultivation, the supernatant of culture is allowed to act on CD4 positive cells (for transduction) and the cultivation is continued for two additional days. The cells are detached from the culture dishes and reseeded into fresh dishes. If the inserted reporter gene is a drug resistance gene, the corresponding drug is added to the culture solution. Following cultivation for several days, the expressability of the reporter gene is analyzed at either a protein or gene level by one of the aforementioned known methods. If drug resistance is utilized in selection, the cells undergoing transduction are observed as colonies, which may be counted to determine the potency of the prepared recombinant HIV vector. The recombinant HIV vectors obtained from the respective clones are compared for potency and the clone having the highest potency is stored as packaging cells.

The thus obtained clone can be utilized for the production of recombinant HIV vectors. The packaging cells described above may be transfected with any vector plasmid by any known method to prepare any recombinant HIV vector such as one to be used in preclinical experiments such as marking or one for use in gene therapy for transferring a drug gene into cells. Alternatively, the packaging cell line may be transfected with a helper plasmid containing a reporter gene in the sequence or cotransfected with a heper plasmid and a reporter gene and selection is made by a method appropriate for the reporter gene, thereby establishing a novel packaging cell line that sustains the vector plasmid stably in cells. The use of this novel packaging line has the advantage of eliminating the need to perform transfection when preparing recombinant HIV vectors.

A specific example of the packaging cells described above is HCN-348 deposited with the National Institute of Bioscience and Human-Technology Agency of Industrial Science and Tehcnology, 1–3, Higashi 1-chome, Tsukuba-shi, Ibaraki-ken, Japan and which was transferred from the original deposit on Mar. 15, 1995 under Accession Number FERM P-14834 to the international deposit on Mar. 11, 1996 under Accession Number FERM BP-5467 under the Budapest Treaty.

The following examples are provided for the purpose of further illustrating the present invention but are in no way to be taken as limiting.

EXAMPLE 1

(Constructing Plasmids)

All procedures for constructing plasmids were in accordance with common procedures of gene recombinant technology. FIG. 1 shows the structure of helper plasmid CGPE (–); gag, pol and env genes sequenced in a wild HIV genome were flanked upstream thereof by a cytomegalovirus derived promoter (CMV) sequence for driving these genes, and a neomycin resistance reporter gene (neo) and a promoter of human simplex herpes virus derived thymidine kinase (TK) were inserted downstream of the gag, pol and env genes, and the group of such genes was incorporated into an expression vector containing an ampicillin resistance gene (amp) and an SV40 replication origin (SV40ori), thereby constructing helper plasmid CGPE(–).

Figure 2:
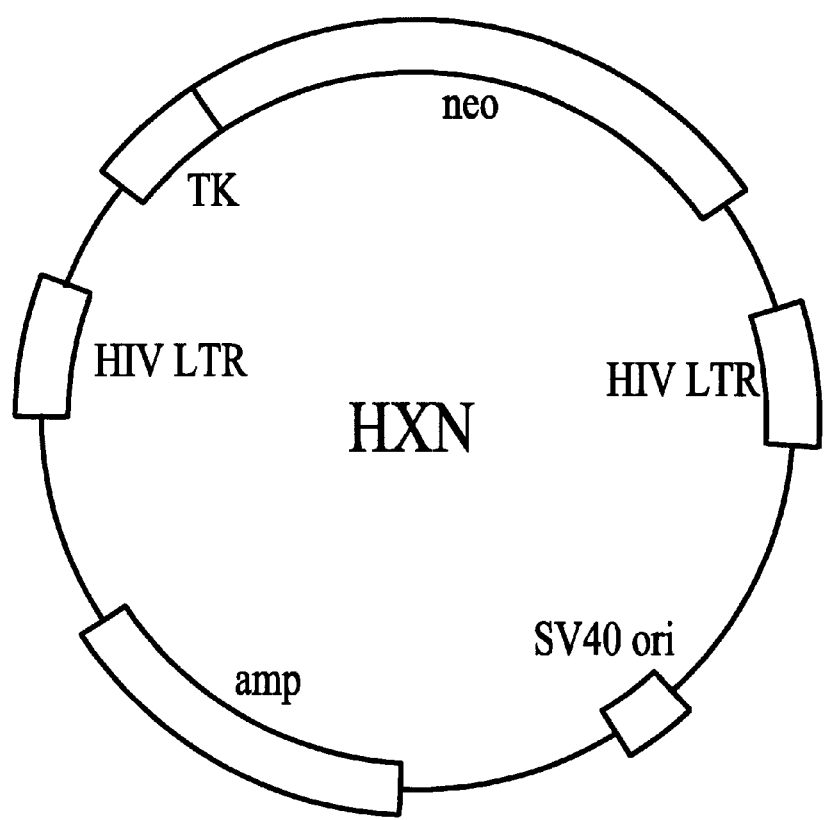
FIG. 2 is a diagram showing the structure of vector plasmid HXN.

FIG. 2 shows the structure of vector plasmid HXN; gag, pol and env genes were deleted from a wild HIV genomic sequence, and a neomycin resistance reporter gene (neo) was inserted into the vacant region, which was flanked upstream thereof by a human simplex herpes virus derived thymidine kinase (TK) as a promoter for driving the neo, and the group of such genes was incorporated into an expression vector containing an ampicillin resistance gene (amp) and an SV40 replication origin (SV40ori), thereby constructing vector plasmid HXN.

EXAMPLE 2

(Transfecting HeLa Cells with Helper Plasmid and Selecting Transfectants by Drug)

Transfection was performed by the usual calcium phosphate procedure. To 10 µg of the CGPE(–) prepared in accordance with Example 1, sterile purified water and a calcium chloride solution were added to make a total of 0.5 mL. The liquid mixture was added dropwise to an HBSP buffer solution (0.5 mL) under shaking and left to stand at room temperature for 30 min to give a plasmid-calcium phosphate coprecipitate. In a separate step, HeLa cells were cultivated in 9-cm dishes to about 50% confluence. The coprecipitate was added to the culture solution, which was incubated for 4 h in a $CO_2$ incubator; thereafter, the culture solution was replaced by a fresh one and subjected to incubation for two additional days. Subsequently, in order to select only the transfectants which sustained the exogenous gene stably in the cells, neomycin analogue G418 was added to the culture solution to give a final concentration of 1,000 µg/mL and incubation was continued for 10 days. The surviving cell populatinos (colonies) were separated one by one and subjected to further incubation in a fresh culture solution containing G418 at a concentration of 1,000 µg/mL, thereby yielding neomycin resistant cell lines.

EXAMPLE 3

(Primary Screening: Quantification of p24 Protein by ELISA)

Figure 3:
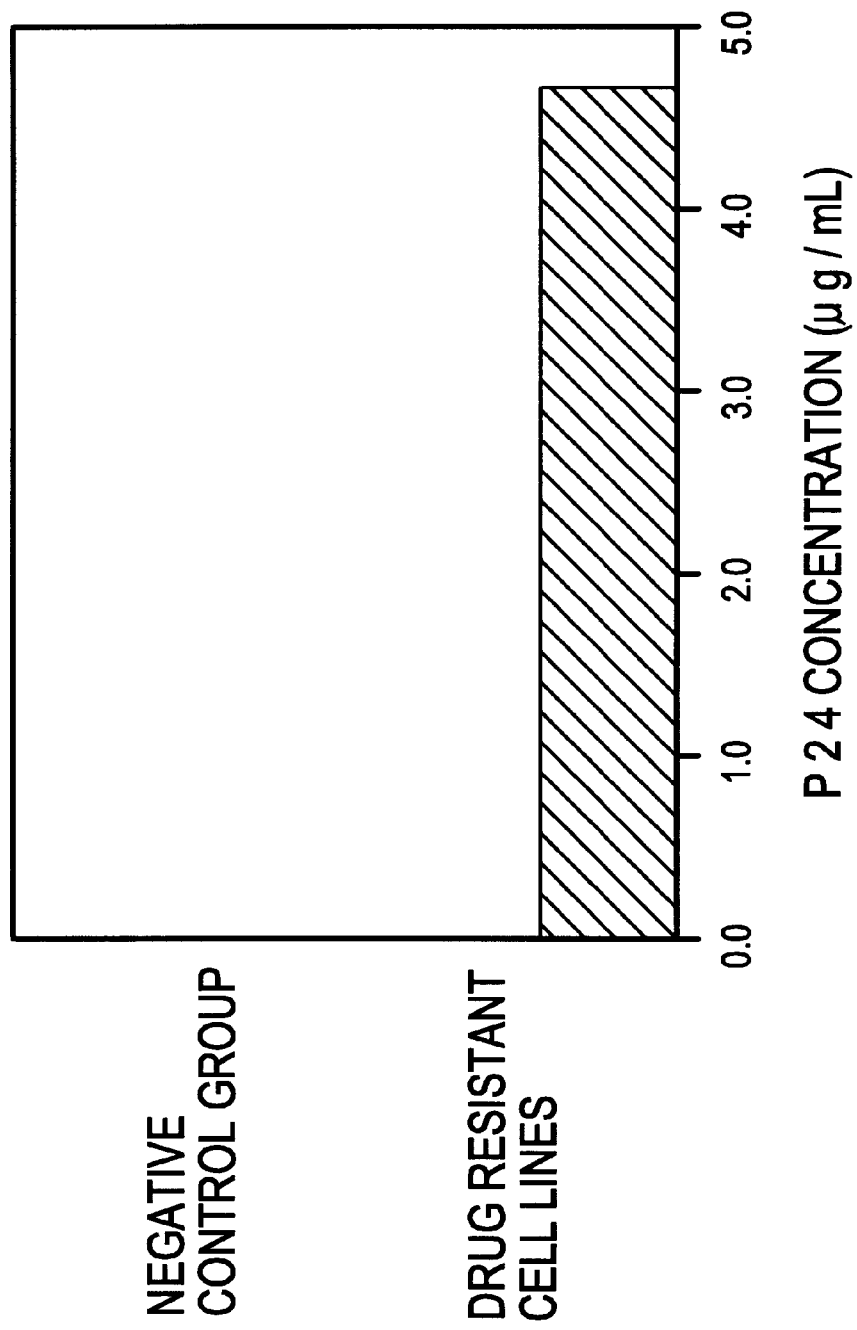
FIG. 3 is a graph showing the results of ELISA quantification (primary screening) of p24 protein contained in the supernatants of cultures of neomycin-resistant cell lines and a negative control group.

The neomycin resistant cell lines obtained in Example 2 were seeded into 3.5-cm culture dishes and cultivated for 2 days. The supernatant of each culture was separated and the concentration of p24 protein in the supernatant was quantified by an ELISA method. Quantification was also made for a negative control group, which was HeLa cells that were not subjected to the procedures of Examples 1 and 2. The results are shown in FIG. 3. The cell lines which were found to be p24 positive by the primary screening were stored for secondary screening.

EXAMPLE 4

(Secondary Screening: Preparing Recombinant HIV Vectors and Assaying Their Potency)

Figure 4B:
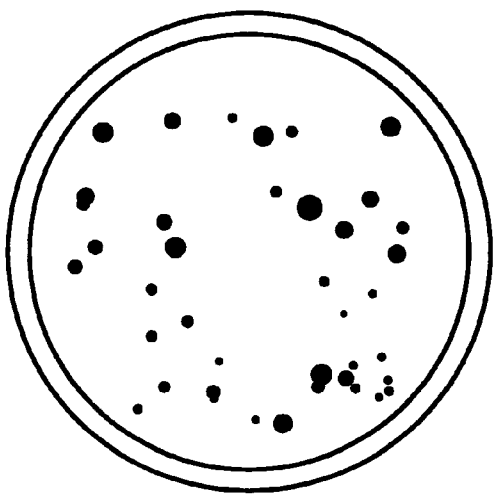
FIG. 4 shows diagrammatically the results of secondary screening.
Figure 4A:
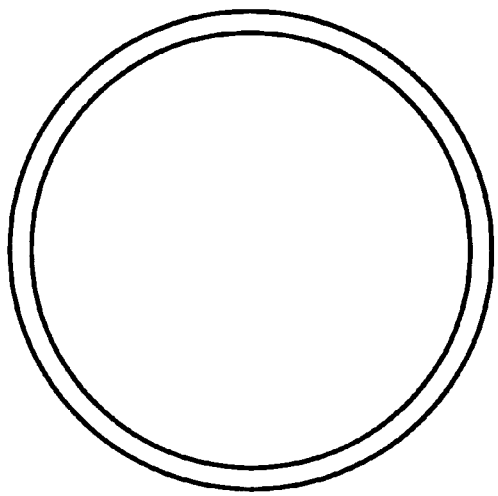

The cell lines selected by primary screening in Example 3 were seeded in 9-cm culture dishes and cultivated to 50% confluence. Each of the cultivated cell lines was transfected with 10 µg of vector plasmid HXN (see FIG. 2) by a calcium phosphate procedure. Following 2-day cultivation, the supernatant of culture was transferred into a centrifugal tube and centrifuged at 2,000 rpm for 10 min. A portion (3 mL) of the resulting liquid supernatant was separated and mixed with 3 mL of a fresh culture solution; the mixture was allowed to act on CD4 positive HeLa cells cultured to 50% confluence. The same procedure was applied to a negative control group, which were HeLa cells that were not subjected to the procedures of Examples 1 and 2. Following 2-day cultivation, the cells were detached by means of a mixture of trypsin and EDTA, suspended in a fresh culture solution containing 1,000 µg/mL of G418 and reseeded into 9-cm dishes. After 10-day cultivation, the resulting colonies were stained with crystal violet (see FIG. 4). No recognizable colonies formed in the negative control group whereas the cell lines obtained in Example 3 produced recognizable colonies; it was thus demonstrated that the cell lines of the present invention function as packaging cells for preparing recombinant HIV vectors.

Industrial Applicability

The human immunodeficiency virus producing cells of the invention are capable of large-scale and consistent preparation of HIV vectors more efficiently than in the prior art.

We claim:

1. A recombinant human immunodeficiency virus producing cell that is obtained by introducing into HeLa cells a recombinant human immunodeficiency virus helper plasmid containing at least the sequences of gag, pol and env genes encoded by a human immunodeficiency virus genome and the promoter sequence inserted upstream of the sequences of the gag, pol and env genes, and being deficient of a packaging signal, and which sustains said genes stably.

2. The recombinant human immunodeficiency virus producing cell of claim 1 wherein the helper plasmid contains a reporter gene.

3. The recombinant human immunodeficiency virus producing cell of claim 1 wherein the helper plasmid is introduced by a calcium phosphate procedure.

4. The recombinant human immunodeficiency virus producing cell of claim 1 which has the Accession Number FERM BP-5467.

5. A process for establishing the recombinant human immunodeficiency virus producing cell of claim 1, which comprises introducing into HeLa cells a recombinant human immunodeficiency virus helper plasmid containing at least the sequences of gag, pol and env genes encoded by a human immunodeficiency virus genome and the promoter sequence inserted upstream of the sequences of the gag, pol and env genes.

6. A process for establishing the recombinant human immunodeficiency virus producing cell of claim 1, which comprises introducing into HeLa cells;

a recombinant human immunodeficiency virus helper plasmid containing at least the sequences of gag and pol genes encoded by a human immunodeficiency virus genome and the promoter sequence inserted upstream of the sequences of the gag and pol genes; and a recombinant human immunodeficiency virus helper plasmid containing at least the sequences of env gene encoded by a human immunodeficiency virus genome and the promoter sequence inserted upstream of the sequences of the env genes.

7. A process for establishing the recombinant human immunodeficiency virus producing cell of claim 1, which comprises introducing into HeLa cells;

a recombinant human immunodeficiency virus helper plasmid containing at least the sequences of gag gene encoded by a human immunodeficiency virus genome and the promoter sequence inserted upstream of the sequences of the gag gene;

a recombinant human immunodeficiency virus helper plasmid containing at least the sequences of pol gene encoded by a human immunodeficiency virus genome and the promoter sequence inserted upstream of the sequences of the pol gene; and a recombinant human immunodeficiency virus helper plasmid containing at least the sequences of the env gene encoded by a human immunodeficiency virus genome and the promoter sequence inserted upstream of the sequences of the env gene.

8. The cell of claim 1, wherein said promoter sequence is a B19 derived promoter.

9. The cell of claim 1, wherein said promoter sequence is a cytomegalovirus derived promoter.

10. The cell of claim 1, wherein said promoter sequence is a human herpes simplex virus derived thymidine kinase.

* * * * *